United States Patent [19]

Moore et al.

[11] 4,105,798
[45] Aug. 8, 1978

[54] PERFLUORO POLYCYCLIC COMPOUNDS FOR USE AS SYNTHETIC BLOOD AND PERFUSION MEDIA

[75] Inventors: Robert E. Moore, Wilmington, Del.; Leland C. Clark, Jr., Cincinnati, Ohio

[73] Assignees: Sun Ventures, Inc., Radnor, Pa.; Children's Hospital Medical Center, Cincinnati, Ohio

[21] Appl. No.: 826,288

[22] Filed: Aug. 22, 1977

Related U.S. Application Data

[63] Continuation-in-part of Ser. No. 706,315, Jul. 19, 1976, abandoned, which is a continuation-in-part of Ser. No. 579,766, May 22, 1975, abandoned, which is a continuation-in-part of Ser. No. 530,791, Dec. 9, 1974, abandoned.

[51] Int. Cl.$^2$ ............... A61K 31/025; C12B 3/00; C12B 9/00
[52] U.S. Cl. ................................. 424/352; 195/1.7; 195/1.8
[58] Field of Search ............... 424/352; 195/1.7, 1.8

[56] References Cited

U.S. PATENT DOCUMENTS 3,823,091  7/1974  Minoo et al. ............ 424/350
3,911,138  10/1975  Clark ...................... 424/352

OTHER PUBLICATIONS

Chem. Abst. Subject Index—vol. 80 (1974), p. 155 GS.

*Primary Examiner*—Sam Rosen
*Attorney, Agent, or Firm*—J. Edward Hess; Donald R. Johnson; Stanford M. Back

[57] ABSTRACT

Novel emulsions of non-aromatizable perfluorinated compounds are useful as blood substitutes or as perfusion materials for the storage of organs such as kidneys prior to transplant. The compounds employed are polycyclic compounds and emulsions prepared from the perfluorinated derivatives thereof possess extremely high stability, zero or extremely low ultimate residue in the body, and a vapor pressure which is just about right for use in the body without adverse effects thereon.

26 Claims, No Drawings

PERFLUORO POLYCYCLIC COMPOUNDS FOR USE AS SYNTHETIC BLOOD AND PERFUSION MEDIA

CROSS REFERENCE TO RELATED APPLICATIONS

This application is a continuation-in-part of application Ser. No. 706,315 filed July 19, 1976, which in turn is a continuation-in-part of application Ser. No. 579,766, filed May 22, 1975, which in turn is a continuation-in-part of application Ser. No. 530,791, filed Dec. 9, 1974 and all now abandoned.

BACKGROUND OF THE INVENTION

The need for synthetic blood is well known. Blood is becoming increasingly expensive, it is perishable, it must be matched to the blood type of the recipient and the transfusion itself can cause hepatitis if rigid procedures are not followed. In addition, blood donations tend to be somewhat seasonal and they often do not coincide with the generally random demands therefor.

A synthetic blood must have several characteristics. Initially, and quite obviously, it must have high oxygen and carbon dioxide solubility since its principal function is to transport oxygen and carbon dioxide. A synthetic blood also must be non-toxic and in this respect it is desirable that when the synthetic blood is replaced by natural blood there is no residue of the former left in vital body organs.

Another characteristic of blood substitutes is that they must have certain vapor pressure requirements. The blood substitutes leave the body by being exhaled and by vaporization through the skin. Preferably the substitute leaves the body at about the same rate that new natural blood is being generated by the body. If the vapor pressure of the substitute is too low it stays in the body too long, wheres if it is too high it evaporates throughout the body's surface and may create problems akin to the "bends".

Blood substitutes must also be capable of forming very stable emulsions with this capability being even more important with perfusion materials. Fluorocarbons are usually immiscible with blood and if used alone could cause embolisms. This problem is overcome by using it in an aqueous emulsion and obviously the emulsion should not separate in use or storage. In connection with perfusion materials this stability is even more strict because the oxygenators used to add oxygen to the perfusion material may catalyze emulsion breakdown. Another reason aqueous emulsions are employed is that salts are added to the water in order to maintain the body salt balance.

The Green Cross Corporation, Osaka, Japan, has published a pamphlet dated Sept. 11, 1974 on perfluoro emulsions as oxygen and carbon dioxide carriers Also Clark et al. report on some of the compounds described in the present invention in Microvascular Research, Volume 8/3, 1974, also presented at the Oxygen Transport to Tissue Symposium, Atlantic City, N.J., Apr. 11, 1974. Certain of the subject matter of this latter article is also taught in U.S. Pat. No. 3,911,138 issued Oct. 7, 1975 to Clark which broadly describes cyclic perfluorohydrocarbons useful as blood substitutes and the like.

The blood substitute and perfusion material of choice as described by these articles is perfluorodecalin. It has a number of desirable properties, but the compounds of the present invention are unexpectedly superior to perfluorodecalin in several respects, in particular emulsion stability, reduced liver retention time, and low toxicity, as described in detail below.

SUMMARY OF THE INVENTION

The novel blood substitutes and perfusion compounds of our invention are non-aromatizable perfluorinated polycyclic compounds having 9–18 carbon atoms and at least two bridgehead carbon atoms linked through a bridge containing at least one carbon atom. They have high oxygen solubility, very low body residue, form very stable emulsions, and have a very satisfactory vapor pressure for one or both uses.

DETAILED DESCRIPTION OF THE INVENTION

The non-aromatizable polycyclic perfluoro compounds suitable for the present purpose are those having two bridgehead carbon atoms linked through a bridge containing at least one carbon atom. By the term bridgehead carbon atom is meant a carbon atom bonded to three other carbons in a cyclic compound having 2 or more rings. By the term "non-aromatizable" is meant a polycyclic perfluoro compound whose ring structure cannot be aromatized without destruction of its original carbon-to-carbon cyclic bonds. Thus, the perfluoro compounds of this invention are to be further distinguished from the perfluorodecalin above mentioned or other similar compounds which can be aromatized. This invention thus employs the perfluoro derivatives of such $C_9$–$C_{18}$ polycyclic compounds as bicyclononanes (e.g. bicyclo[3.3.1]nonane, 2,6-dimethylbicyclo[3.3.1]nonane or 3-methylbicyclo[3.3.1]nonane), adamantane, methyl and dimethyladamantane, ethyladamantane, tetrahydrodicyclopentadiene, methyl and dimethylbicyclooctanes, ethylmethyladamantane, ethyldimethyladamantane, tetrahydrobinor-S, methyldiadamantane, triethyladamantane, trimethyldiadamantane, ethyldimethyldiadamantane, pinane, camphane, 1,4–6, 9-dimethanodecalin, bicyclo[4.3.2]undecane, bicyclo[5.3.0]decane and the like, or mixtures thereof. They can be made by known means. Preferably the polycyclic contains 9–12 carbon atoms and it generally will have not more than four rings, usually 2–3 rings.

As synthetic blood, $C_8$ materials (in perfluorinated form) have too high a vapor pressure to be useful. The $C_{10}$ and $C_{11}$ materials are just about right whereas the $C_9$s are a little on the high side re vapor pressure and the $C_{12}$s are a little on the low side. $C_{10}$ and $C_{11}$ materials have atmospheric boiling points between about 125°–165° C and this is a satisfactory criteria, with the preferred range between 125° and 145° C. This preferred range will be mostly $C_{10}$ materials.

It should be noted that even though $C_{12}$s are not suitable as blood substitutes they, and up to $C_{18}$s, can be used as perfusion compounds as in this application vapor pressure is not as important. Above $C_{18}$ the oxygen solubility of the material is generally too low.

The polycyclic material is used in perfluorinated form. For the present purpose the term perfluorinated includes $C_9$–$C_{18}$ polycyclics which are at least 95% by weight completely fluorinated (i.e., perfluorinated in the strict sense), preferably at least 98% and more preferably 100%. In all cases of less than 100% the balance will of course be highly fluorinated.

The fluorination is carried out by known means. For example, the hydrocarbon or partially fluorinated hydrocarbon is passed slowly over a bed of $CoF_3$ containing 2–3 times the stoichiometric amount of fluorine at 250°–275° C which effects partial fluorination. The procedure is then repeated at 300°–350° C to effect complete fluorination of all but a few percent impurities which are both saturated, partially fluorinated compounds and olefinic fluorocarbons. The former boil at least 10° C higher than the desired perfluoro compound and are removed by distillation. The latter boil at essentially the same temperature so they are extracted with an amine such as diethylamine (DEA). Residual amine is removed with concentrated $H_2SO_4$. Residual acid is removed with 1% $NaHCO_3$ solution which is then extracted with acetone. Finally, residual acetone is distilled off.

It has been found that in some instances, vigorous perfluorination of the cyclic hydrocarbon results in partial ring-opening of the starting material, with the result that the perfluorinated product may actually be a mixture of some of the above-described polycyclic materials. Thus, for example, the perfluorination of methyladamantane by known means, principally involving, for example, $CoF_3$ as the perfluorinating agent, provides a mixture of perfluorodimethylbicyclo [3.3.1]nonane and perfluoromethyladamantanes, while the corresponding product of dimethyladamantane is perfluorotrimethylbicyclo [5.3.0]nonane and perfluorodimethyladamantane. Similarly, perfluorination of tetrahydrodicyclopentadiene yields perfluorobicyclo [5.3.0]decane and perfluorotetrahydrodicyclopentadiene. These compounds of these mixtures may be separated by conventional means, as for example by distillation, chromatographic techniques and the like, and formulated individually. If desired, the mixtures themselves may be used instead in the blood formulations.

Alternatively, as described in copending application Ser. No. 771,873, filed Feb. 25, 1977, in the name of Robert E. Moore and incorporated herein by reference, when the polycyclic hydrocarbon is first partially fluorinated under mild conditions with fluorinating agents other than $CoF_3$ followed by vigorous perfluorination, with, e.g. $CoF_3$ little if any ring-opening results, and a substantially pure perfluorinated product corresponding essentially to the said hydrocarbon starting material is obtained for use in the described formulations.

The perfluoropolycyclic is employed as a water emulsion containing more than 40% water by volume. Preferably the emulsion contains 10–30 volume percent of the perfluoropolycyclic. Normally the emulsion will contain 1–5 volume percent of an emulsifier. The specific emulsifier employed is not critical but it should itself be nontoxic and should form a stable emulsion. The preferred emulsifier is a yolk-phospholipid as this is well known to be harmless in the body. Also suitable for perfusion purposes are the polyoxyethylenes and polyoxypropylenes available commercially as "Pluronics". "Pluronic F-68" has a molecular weight of 8350 and forms a very stable emulsion. However, it has been reported that "Pluronic" type materials precipitate plasma protein and hence they are preferably limited to perfusion, with the commercially available yolk-phospholipids used for blood substitutes.

The emulsion can be formed with conventional high shear emulsifiers such as the Manton-Gaulin homogenizer. Typically, the particle size of the perfluoropolycyclic in the emulsion is 0.001–10 microns, frequently 0.01–10 micron, usually 0.05–0.5 micron and preferably 50 weight percent of the particles have diameters of 0.05–0.3 micron. As is well known the particle size can be adjusted by the amount of shear employed. The smaller particle size is preferred since it has been found that the resulting emulsions are more stable as particle size is reduced.

As indicated above, retention of the material in the body is important. The data below compare perfluorinated tributylamine (PFTBA), decalin (PFD), and methyldecalin (PFMD), with certain of the perfluorinated polycyclic hydrocarbons of this invention which have been obtained by perfluorinating the said polycyclic materials with just $CoF_3$. Thus, in the table below "PFDMA" is the perfluorinated product derived from dimethyladamantane, i.e. a mixture of perfluorotrimethylbicyclo [3.3.1]nonane containing about 25 percent of other materials, principally perfluorinated dimethyladamantane. "PFMA" is the perfluorinated product of methyladamantane i.e., a mixture of perfluorodimethylbicyclo [3.3.1]nonane containing an unidentified amount of other compounds including perfluoromethyladamantane. Finally, "PFTHDCP" is the product of tetrahydrodicyclopentadiene, i.e. perfluorobicyclo [5.3.0] decane containing about 50 percent of other materials, principally perfluorotetrahydrodicyclopentadiene.

Emulsions containing 10% of the material to be tested, surfactant and water are made up and tested in the manner specified in *Science*, Vol. 181, August 1973, page 681. Mice were injected with the various emulsions. The mice were killed at intervals thereafter, the liver analyzed, and the percentage of original amount of PF material injected and still in the liver was determined. The data below show these results.

| Material | Percent of Dose in Liver After Stated Weeks | | | |
|---|---|---|---|---|
| | 2 | 6 | 12 | 20 |
| PFD | 4 | 2 | 2 | — |
| PFMD | 30 | 19 | 2 | 2 |
| PFTBA | 38 | 30 | 30 | 30 |
| PFDMA | 35 | 28 | 23 | 2 |
| PFMA | 7 | 1 | — | — |

It is apparent that the PFMA (which had a small amount of higher boiling impurity which retards its release from the body) is as good or better than PFD. Even the PFDMA gets down to the 2% level of the PFD but it does take longer.

The corresponding results of the liver and spleen analysis of mice infused at 150 cc/kg with PFTHDCP was as follows:

| TIME FROM INFUSION | % IN LIVER | % IN SPLEEN |
|---|---|---|
| 3 wks. | 15.21 | 6.71 |
| 3 wks-6 days | 3.83 | 3.38 |

The relative stability of a PFDMA emulsion and PFMA is excellent in that it is stable indefinitely, (e.g., over 6 months) at 4°–7° C whereas the PFD emulsion breaks down in several days at room temperature and in several weeks at 4°–7° C. PFTBA is also excellent. See for example the *Journal of Microvascular Research*, August 1974. In addition to emulsion stability, emulsion prepared from PFDMA and PFD (in the same manner) show optical densities of 0.1 and 0.4 respectively, which means that it forms a transparent emulsion in contrast to a 2.2 optical density obtained with PFTBA. The latter emulsion is very milky in appearance, indicating a larger particle size.

It has also been found that our perfluorinated materials are very nontoxic. The $LD_{50}$ after infusion (ml/kg) of our materials compared with others are follows:

| Emulsion | $LD_{50}$ | | |
|---|---|---|---|
| | 1 Hr. | 3 Days | 7 Days |
| 10.9% PFD | 190 | 160 | 159 |
| 10 % PFDMA | 200 | 175 | 175 |
| 5 % PFMA | 200 | 200 | 200 |
| 10 % PFTBA | 200 | 120 | 120 |

As noted above the perfluorinated materials of the invention have high oxygen and carbon dioxide solubility. For example the perfluorinated materials can normally contain about 40–60 cc oxygen per 100 cc fluorocarbon and the carbon dioxide solubility is about twice this. Normally blood will absorb about 20 cc oxygen per 100 cc of blood with carbon dioxide solubility being twice that of oxygen. The compositions of our invention will normally contain 30–60 cc of oxygen per 100 cc of the perfluorinated material but ratios as low as 10 cc per 100 cc can be used, and higher amounts such as 100 cc per 100 cc can be used where available. All the foregoing solubilities are at 25° C and 760 milliliters mercury. The compounds in the higher end ($C_{12}$–$C_{18}$) of the $C_9$–$C_{18}$ carbon atom range perform in the manner described above except that their oxygen solubility decreases. Above $C_{18}$ the solubility is not high enough to make these compounds practical candidates.

EXAMPLE 1

Tetrahydrodicyclopentadiene (24.15 g) was pumped at 0.494 cc/min through a stirred horizontal $CoF_3$ bed which was thermally graded from 200° to 250° C between the inlet and outlet respectively. The crude product weighed 63.6g. This product was dried over mole sieves and 55.8g was passed through the reactor for a second time. The reactor was thermally graded from 300° to 375° C. during this second pass. The crude product from the second pass weighed 60.8g for an 87% yield.

Gas chromatographic analysis showed a mixture containing about 35% perfluorotetrahydrodicyclopentadiene and 50% perfluorobicyclo [5.3.0] decane.

The mixture was then water-washed to remove residual HF. If was then refluxed with aqueous KOH(10%) for 1 hour, and dried over mole sieves. This product was then distilled to remove light and heavy ends, followed by processing by preparative gas chromatography (½ inch × 42 feet 20% SE 30 in 30/60 Chromosorb P). Each of the identified components of the mixture was isolated in > 98% purity. The components were then each exhaustively extracted with diethylamine until no further discoloration was observed.

EXAMPLE 2

In accordance with the procedures of Example 1, methyladamantane (10 g), dissolved in 10cc n-hexane, was pumped through the $CoF_3$ reactor, thermally graded from 225° C to 275° C, at 0.247 cc/min. The crude product, which weighed 26.7g, was dried over mole sieves dissolved in perfluoro n-heptane (5cc), and passed through the rector a second time at 0.494 cc/min. The reactor was graded from 250° C to 350° C for the second pass.

Gas chromatographic analysis showed a mixture containing ~ 5% perfluoromethyladamantane and > 90% perfluorodimethylbicyclo [3.3.1] nonane.

The mixture ws then separated in accordance with the procedures of Example 1 to yield each of the identified products in high purity.

EXAMPLE 3

In accordance with the procedures of Example 1, 1,3-dimethyladamantane (18g) was pumped through the $CoF_3$ reactor, held at 250° C in all 4 zones, at 0.247 cc/min. The crude product, which weighted 53.5g, was dried over mole sieves and passed through the reactor again at 0.382 cc/min. During the second pass the reactor zones were thermally graded from 225° to 325° C. The crude product, which weighted 50.2g (85% yield) was analyzed by gas chromatography and showed to be a mixture containing ~ 5% perfluorodimethyladamantane and > 90% perfluorotrimethylbicyclo [3.3.1]nonane.

The mixture was then separated in accordance with the procedures of Example 1 to yield each of the identified products in high purity.

The following examples, disclosed in co-pending application Ser. No. 771,873 (supra), illustrate an alternate method for preparing the perfluoro polycyclic materials used in the emulsions of this invention, wherein there are employed partially fluorinated polycyclic hydrocarbons as intermediates in the preparation of substantially pure perfluorinated materials.

In particular, the following four examples demonstrate the preparation of partially fluorinated adamantanes which may then be perfluorinated in accordance with Example 8.

EXAMPLE 4

Adamantane dicarboxylic acid (22.4g-0.1 mole) and $SF_4$ (27.0g-25% excess) were heated in a hoke bomb for 24 hours at 110° C. The contents of the pressure vessel were cooled, extracted with $CCl_4$, filtered and the $CCl_4$ evaporated off. The residue consisted of 21.8g of bistrifluoromethyl adamantane (80% yield).

EXAMPLE 5

2-adamantanone (15.0g-9.1 mole) and $SF_4$ (13.g-25% excess) were heated as in Example 1. The product was worked up as described in Example 1 to give 12.9g of 2,2-difluoro adamantane (75% yield).

EXAMPLE 6

5,7-dimethyl-1,3-adamantane dicarboxylic acid (25.2g-0.1 mole) and $SF_4$ (27.0g-25% excess) were heated and worked up as in Example 1 to give 18g of 3,5-dimethyl-5,7-bis(trifluoromethyl) adamantane (60%).

EXAMPLE 7

1,3-dimethyl adamantane (42g) is added slowly to a slurry of $MnF_3$ (1 lb) in perfluoro 1-methyl decalin. After all the hydrocarbon has been added the mixture is heated with rapid stirring to 200° C for 24 hours, and the product extracted with Freon 113 and distilled to remove both the Freon 113 and perfluoro 1-methyl decalin. The distillation residue consists of partially fluorinated 1,3-dimethyl adamantane in which the average molecule contains approximately 8 fluorine atoms; e.g. $C_{12}H_{12}F_8$.

EXAMPLE 8

Bistrifluoromethyl adamantane (24cc; 33.67g; 0.123 moles) from Example 4 was charged into a preheater at 0.247cc/min. The preheater temperature was 250° C, and in the CoF$_3$ reactor divided into four heating zones, the temperature was graduated from 250° C in Zone 1 to 300° C in Zone 4. The product line was kept at 225° C. After all the hydrocarbon had been charged to the reactor, the reactor was purged with nitrogen for 3.25 hours. The crude product weighed 46.0g. This material was water washed until the pH of the water was 5.

This material from the second stage was dried over mole sieves overnight and then 45.84g was recharged at a rate of 0.764 cc/min. to the reactor which was graduated from 275° C in Zone 1 to 380° C in Zone 4 for the final stage. The reactor was purged with nitrogen for 4 hours before removing the product receiver containing 47.8g. fluorocarbon; 75% material balance g.c. analysis showed the product contained 90% perfluoro 1,3-dimethyl adamantane, confirmed by mass spectrography and $^{19}$FNMR.

A similar run was made with 1,3-bis(trifluoromethyl)-5,7-dimethyl adamantane to give a 55% yield of perfluoro tetramethyl adamantane.

In a similar fashion 2,2-difluoro adamantane and 3,5-dimethyl-5,7-bis(trifluoromethyl) adamantane of Examples 5 and 6 were reacted with CoF$_3$ in accordance with the procedures of Example 8 to give the corresponding perfluoroadamantanes in high purity and yield.

EXAMPLE 9

Exo-tetrahydrodicyclopentadiene (35 g) is added slowly to a slurry of MnF$_3$ (1 lb) in perfluoro(1-methyl) decalin solvent. After all the hydrocarbon has been added, the mixture is heated to 200° C and stirred rapidly for 24 hours. The product is extracted with Freon 113 and distilled to remove both the Freon 113 and perfluoro (1-methyl) decalin. The distillation residue consists of partially fluorinated tetrahydrodicyclopentadiene in which the average molecule contains approximately 7 fluorine atoms: C$_{10}$H$_9$F$_7$.

When the thus obtained partially fluorinated tetrahydrodicyclopentadiene is then perfluorinated with CoF$_3$ in accordance with the procedures of Example 8, there is obtained substantially pure exo-and endo-perfluorotetrahydrodicyclopentadiene in high yield, and essentially free of by-products.

EXAMPLE 10

In accordance with the procedures of Example 9, but substituting partially fluorinated camphane, hydrogenated pinane, 1,4-methanodecalin or 1,4,5,8-dimethanodecalin for partially fluorinated tetrahydrocyclopentadiene, there is obtained the corresponding perfluorinated cyclocarbon in high yield, and substantially free of any degradation ring-opened by products.

EXAMPLE 11

Fluoroolefins and acetylenes, readily undergo Diels-Alder type reactions to function as dienophiles in 1,4-cyclo-addition reactions; their reactivity towards dienes is generally higher than that of their hydrocarbon analogues. The following examples demonstrate the preparation of partially fluorinated cyclocarbons which may then be exhaustively fluorinated in accordance with the procedures of Example 8 to provide perfluorocyclocarbons in high yield and essentially free of ring-opened by-products:

A. Reaction of cyclopentadiene with hexafluoro-but-2-yne at 100° C for 24 hours gives 2,3-bis (trifluoromethyl) bicyclo [2.2.1] heptadiene which, upon hydrogenation over platinum, gives 2,3-bis(trifluoromethyl) bicyclo [2.2.1] heptane.

B. Also, in a like manner, octafluoro-but-2-ene and cyclopentadiene react to give 2,3-difluoro-2,3-bis(trifluoromethyl) bicyclo[2.2.1] heptane which, after hydrogenation over ruthenium gives 2,3-bis(trifluoromethyl)bicyclo [2.2.1] heptane.

EXAMPLE 12

Norbornadiene (1 mole) and a 25% molar excess of hexafluorocyclopentadiene are heated for 24 hours at 100° C to give

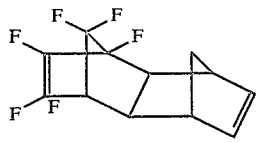

which, after treatment with CoF$_3$ in accordance with the procedures of Example 5 yields highly pure perfluoro 1,4,5,8-dimethanodecalin.

The following examples are included to further illustrate one method for preparing the synthetic blood and perfusion emulsions of this invention from the above-described perfluoro polycyclic compounds.

EXAMPLE 13

To 10 cc perfluorotricyclo [3.3.1] nonane is added 5 gm Pluronic F68 emulsifier. Distilled water is then added to the mixture to form a total volume of 50 cc. The solution is filtered through a 10-micrometer millipore filter, and the solution, which is cooled by an ice bath to about 0°–5° C, is sonicated with an ultrasonic vibrator. During the sonication the optical density of 5 cc samples is measured at regular intervals until a constant optical density value is obtained, signifying that the smallest particle size emulsion possible has been obtained. The sonication is then stopped, and a stable aqueous emulsion of 20% by volume of perfluorotricyclo [3.3.1] nonane is recovered.

EXAMPLE 14

In accordance with the procedures of Example 13, but substituting perfluoromethyladamantane for the nonane compound, and using yoke-phospholipid emulsifier, there is obtained a stable, aqueous emulsion of 20% by volume of perfluoromethyladamantane.

EXAMPLE 15

To 5 cc perfluorotetrahydrodicyclopentadiene is added 25 gm Pluronic F68 emulsifier. Distilled water is then added to the mixture to form a total volume of 500 cc. The solution is filtered through a 10-micrometer millipore filter and the solution homogenized in a Manton-Gaulin homogenizer filtered with a cooler. During homogenization, the optical density of 5 cc samples of emulsion is measured at regular intervals until a constant optical density value is obtained, signifying that the smallest particle size emulsion possible has been obtained. The homogenization is then stopped, and a stable aqueous emulsion of 10% by volume of perfluorotetrahydrodicyclopentadiene is recovered.

EXAMPLE 16

In accordance with the procedures of Example 15, but substituting perfluoromethylbicyclooctane for the cyclopentadiene compound, and using yolk-phospholipid, there is obtained a stable, aqueous emulsion of 10% by volume of perfluoromethylbicyclooctane.

EXAMPLE 17

To 100 cc perfluoroethylbicyclooctane is added 50 gm Pluronic F68 emulsifier. Distilled water is then added to the mixture to form a total volume of 500 cc. The solution is filtered through a 10-micrometer millipore filter and the solution homogenized in a Manton-Gaulin homogenizer filtered with a cooler. During homogenization, the optical density of 5 cc samples of emulsion is measured at regular intervals until a constant optical density value is obtained. The homogenization is then stopped, and a stable, aqueous emulsion by 20% by volume of perfluoroethylbicyclooctane recovered.

EXAMPLE 18

In accordance with the procedures of Example 17, but substituting perfluoroethylmethyladmantane for the bicyclooctane compound, there is obtained a stable, aqueous emulsion of 20% by volume of perfluoroethylmethyladamantane.

EXAMPLE 19

In accordance with the procedure of Example 13, but starting with perfluoroethyldimethyladamantane, there is obtained a stable, aqueous emulsion of 10% by volume of said perfluoroethyldimethyladamantane.

EXAMPLE 20

In accordance with the procedures of Example 13, but substituting perfluorotetrahydrobinor-S for the nonane compound, there is recovered a stable, aqueous emulsion of 20% by volume of said perfluorotetrahydrobinor-S.

EXAMPLE 21

In accordance with the procedures of Example 15, but starting with perfluoromethyldiamantane, and using yolk-phospholipid emulsifier, there is obtained a stable, aqueous emulsion of 10% by volume of said perfluoromethyldiamantane.

EXAMPLE 22

In accordance with the procedures of Example 17, but starting with perfluorotriethyladamantane, there is recovered a stable, aqueous emulsion of 20% by volume of said perfluorotriethyladamantane.

EXAMPLE 23

In accordance with the procedures of Example 13, but using perfluorotrimethyldiamantane and yolk-phospholipid as the emulsifier, there is obtained a stable, aqueous emulsion of a 10% by volume of said perfluorotrimethyldiamantane.

EXAMPLE 24

In accordance with the procedures of Example 15, but using perfluoroethyldimethyldiamantane, there is obtained a stable, aqueous emulsion of a 10% by volume of perfluoroethyldimethyldiamantane.

EXAMPLE 25

In accordance with the procedure of Example 13, but substituting perfluorodimethanodecalin for the nonane compound, and yolk-phopholipid for Pluronic F68, there is obtained a stable, aqueous emulsion of 10% by volume of said perfluorodimethanodecalin.

EXAMPLE 26

In accordance with the procedure of Example 15, but substituting perfluoromethyldimethanodecalin for the nonane compound, there is obtained a stable, aqueous emulsion of 10% by volume of said perfluoromethyldimethanodecalin.

EXAMPLE 27

In accordance with the procedure of Example 13, but substituting perfluorotetrahydromethyldicyclopentadiene for the nonane compound, there is obtained a stable, aqueous emulsion of 10% by volume of said perfluorotetrahydromethyldicyclopentadiene.

EXAMPLE 28

In accordance with the procedure of Example 13, but substituting perfluoroethyladamantane for the nonane compound, and yolk-phospholipid for Pluronic F68, there is obtained a stable, aqueous emulsion of 10% by volume of said perfluoroethyladamantane.

EXAMPLE 29

To 5 cc perfluoroadamantane is added 2.5 gm Pluronic F68 emulsifier. Distilled water is then added to the mixture to form a total volume of 50 cc. The solution is filtered through a 10-micrometer millipore filter; and the solution, which is cooled by an ice bath to about 0°–5° C, is sonicated with an ultrasonic vibrator. During sonication, the optical density of 5 cc samples of emulsion is measured at regular intervals until a constant optical density value is obtained, signifying that the smallest particle size emulsion possible has been obtained. The sonication is then stopped, and a stable, aqueous emulsion of 10% by volume of perfluoroadamantane is recovered.

The invention claimed is:

1. An artificial blood comprising an emulsion of a non-aromatizable perfluorinated material in water, the amount of water being greater than 40% by volume, said emulsion containing a non-toxic emulsifier and a perfluorinated $C_9$–$C_{18}$ polycyclic hydrocarbon containing at least two bridgehead carbon atoms linked through a bridge containing at least one carbon atom.

2. Composition according to claim 1 wherein the amount of said perfluorinated material is 10–30%.

3. Composition according to claim 1 wherein said perfluorinated material contains 9–12 carbon atoms.

4. Composition according to claim 1 wherein said perfluorinated material contains 10–11 carbon atoms.

5. Composition according to claim 1 additionally containing a yolk-phospholipid or poly($C_2$–$C_3$ alkylene oxide) surfactant.

6. Composition according to claim 1 wherein said perfluorinated material has a boiling point of 125°–156° C.

7. Composition according to claim 1 stable for several months at room temperature.

8. Composition according to claim 1 wherein the particle size of the perfluorinated material in the emulsion is from about 0.001 to 10 microns.

9. The composition according to claim 8 wherein the particle size of the perfluorinated material is from about 0.05–0.5 microns.

10. The composition according to claim 9 wherein about 50 weight percent of the particles have diameters of from about 0.05–0.3 microns.

11. Composition according to claim 1 wherein said perfluorinated material is a perfluorinated bicyclononane.

12. Composition according to claim 1 wherein said perfluorinated material is a perfluorinated bicyclooctane.

13. Composition according to claim 1 wherein said perfluorinated material is a perfluorinated adamantane hydrocarbon.

14. Composition according to claim 1 wherein the perfluorinated material is a mixture comprising perfluoromethyladamantane and perfluorodimethylbicyclo[3.3.1]nonane.

15. Composition according to claim 1 wherein the perfluorinated material is a mixture comprising perfluorodimethyladamantane and perfluorotrimethylbicyclo [3.3.1]nonane.

16. Composition according to claim 1 wherein the perfluorinated material is a mixture comprising perfluorotetrahydrodicyctopentadiene and perfluorobicyclo [5.3.0 decane.

17. Composition according to claim 1 additionally containing 10–100 cc $O_2$(25° C, 760 mm Hg) per 100 cc of the perfluorinated material.

18. Composition according to claim 17 wherein said perfluorinated material is perfluorotetrahydrodicyclopentadiene.

19. Composition according to claim 17 wherein said perfluorinated material is a perfluorinated bicyclononane.

20. Composition according to claim 17 wherein said perfluorinated material is a perfluorinated bicyclooctane.

21. Composition according to claim 17 wherein said perfluorinated material is a perfluorinated adamantane hydrocarbon.

22. Composition according to claim 17 wherein the perfluorinated material is a mixture comprising perfluoromethyladamantane and perfluorodimethylbicyclo [3.3.1] nonane.

23. Composition according to claim 17 wherein the perfluorinated material is a mixture comprising perfluorodimethyladamantane and perfluorotrimethylbicyclo [3.3.1] nonane.

24. Composition according to claim 17 wherein the perfluorinated material is a mixture comprising perfluorotetrahydrodicyclopentadiene and perfluorobicyclo [5.3.0] decane.

25. A method for supporting oxygen-carbon dioxide transport in an animal body which comprises the intravascular administration of an artificial blood defined in claim 1.

26. A method for supporting oxygen transfer in an animal organ which comprises externally perfusing the animal organ with an artificial blood defined in claim 1 having oxygen dissolved therein, the perfluorinated material in said blood having a vapor pressure which permits it to leave the organ without causing adverse gas collection in the organ tissue.

* * * * *